United States Patent [19]

Piselli

[11] Patent Number: 4,865,770

[45] Date of Patent: Sep. 12, 1989

[54] PROCESS FOR THE OPTICAL RESOLUTION OF 2-(6-METHOXY-2-NAPHTHYL)PROPIONIC ACID

[75] Inventor: Fulvio L. Piselli, Milan, Italy

[73] Assignee: Industria Chemica Profarmaco S.p.A., Milan, Italy

[21] Appl. No.: 209,291

[22] Filed: Jun. 20, 1988

[30] Foreign Application Priority Data

Jul. 10, 1987 [IT] Italy ................ 21254 A/87

[51] Int. Cl.$^4$ ............................. C07B 57/00
[52] U.S. Cl. .................... 562/402; 562/401; 562/466
[58] Field of Search ........... 562/402, 466, 401; 260/501.1

[56] References Cited

U.S. PATENT DOCUMENTS 4,376,213  3/1983  Nohira et al. ............ 562/401
4,417,070  11/1983  Arai et al. ............ 562/401 X Primary Examiner—Werren B. Lone
Assistant Examiner—Vera C. Clarke
Attorney, Agent, or Firm—Walter H. Schneider

[57] ABSTRACT

A process for the optical resolution of 2-(6-methoxy-2-naphthyl)propionic acid by seeding a supersaturated solution of the ethylamine salt of said acid.

6 Claims, No Drawings

PROCESS FOR THE OPTICAL RESOLUTION OF 2-(6-METHOXY-2-NAPHTHYL)PROPIONIC ACID

The present invention relates to a process for the optical resolution of 2-(6-methoxy-2-naphthyl) propionic acid enantiomers.

2-(6-methoxy-2-naphthyl) propionic acid, which is also known under the denomination of Naproxen, has been used in human therapy for a long time, due to its antiinflammatory properties.

More precisely, only the dextrorotatory isomer, which is markedly more active than the racemic mixture, is used.

Thus, different processes for the resolution of racemic Naproxen, by means of optically active bases such as cinchonidine, α-phenylethylamine, N-methyl-glucamine, have been described.

On the contrary, methods based on the supersaturation phenomenon are not known, said methods, if applicable, avoiding the use of optically active bases, which are generally expensive, and the requirement of repeated fractional crystallizations, which involve a decrease in the yields of the desired enantiomer.

Now it has been found that 2-(6-methoxy-2-naphthyl) propionic acid ethylamine salt can be resolved into its enantiomers by means of preferential crystallization, by seeding a saturated solution with one of the separated isomers of said salt.

Separation of optical isomers is made possible by the supersaturation phenomenon (which is already known and described in literature, see G. Amiard, Bull. Soc. Chim. Fr. 1956, 447; L. Velluz, G. Amiard, R. Joly, Bull. Soc. Chim. Fr. 1953, 342; L. Velluz, G. Amiard, Bull. Soc. Chim. Fr. 1953, 903; G. Amiard, Experienta 1959, 15, 38) of the two isomers present in the solution and by the consequent preferential precipitation of one of said isomers, until normal saturation conditions, which restore the equilibrium state in the system, are attained. Supersaturation conditions for the opposite isomer are then restored, as well known in the art, by addition of an amount of the racemic salt equivalent to the first precipitate. A second precipitate of the opposite isomer will thus be obtained, and the cycle will be repeated as many times as desired, obtaining the dextrorotatory isomer, whereas levorotatory isomer will be racemized by known methods.

According to the invention, supersaturated solutions of 2-(6-methoxy-2-naphthyl) propionic acid can be obtained using as solvents acetone or methanol containing 4 to 20% of water. Particularly preferred is the use of acetone containing 15 to 18% of water.

Supersaturation conditions are reached at temperatures above 40° C., whereas precipitation due to the addition of the dextrorotatory acid salt takes place at a temperature depending on the water content of the solvent mixture and which is generally from 20° to 40° C.

In the preferred case, precipitation was observed at about 30°–35° C., whereas, in case of higher water percentages, precipitation will require lower temperatures.

Thus, by addition to the filtrate of a racemic salt amount equivalent to the obtained precipitate, and subsequent cooling, an equal amount of levorotatory salt will precipitate.

By filtration of the new precipitate and new addition of the racemic salt, always in an amount equal to the obtained precipitate, dextrorotatory salt crystallizes again.

Such a method, repeated in continuous cycles, allows to separate the optically pure dextro salt, from which the acid can be obtained by treatment with a mineral acid.

The following examples further illustrate the invention without limiting it.

EXAMPLE 1

(a) Preparation of (±)-2-(6-methoxy-2-naphthyl)propionic acid ethylamine salt 230 g (1 mole) of (±)-2-(6-methoxy-2-naphthyl) propionic acid was dissolved in 1.5 l of acetone at about 45° C. By addition of 64 g (1 mole) of a 70% w/w aqueous monoethylamine solution, the ethylamine salt crystallized. The mixture was cooled to about 25° C., filtered and washed portionwise with 200 ml of acetone.

247 g of the product was obtained, i.e. 90% on theoric.

(b) Resolution (±)-2-(6-methoxy-2-naphthyl) propionic acid ethylamine salt 400 g (1.45 mole) of (±)-2-(6-methoxy-2-naphthyl) propionic acid ethylamine salt was dissolved at about 45° C. in 2 l of acetone containing 16% w/v of water.

30 g (0.11 mole) of (±)-2-(6-methoxy-2-naphthyl) propionic acid ethylamine salt was added and the mixture was stirred till complete dissolution. After cooling to about 35° C., crystallization was seeded by means of 1 g of (+)-2-(6-methoxy-2-naphthyl) propionic acid ethylamine salt and the mixture was slowly stirred for 2 hours, carefully cooling so as to keep temperature to about 30° C. The obtained crystals were filtered and washed with 100 ml of acetone. 60 g of (+)-2-(6-methoxy-2-naphthyl) propionic acid ethylamine salt having an optical purity higher than 90% was obtained.

Acetone mother liquors were heated to about 45° C., added with 60 g of (±)-2-(6-methoxy-2-naphthyl) propionic acid ethylamine salt and stirred till complete dissolution.

After cooling to 35° C., 1 g of (−)-2-(6-methoxy-2-naphthyl) propionic acid ethylamine salt was added, with slowly stirring for 2 hours and carefully cooling so to reach a temperature of about 30° C. The obtained crystals were filtered, washing portionwise with 100 ml of acetone. 60 g of (−)-2-(6-methoxy-2-naphthyl) propionic acid ethylamine salt was obtained, having an optical purity higher than 90%.

Acetone mother liquors were added again with 60 g of (±)-2-(6-methoxy-2-naphthyl) propionic acid ethylamine salt and heated to 45° C. till complete dissolution.

After cooling to 35° C. and seeding with 1 g of (+)-2-(6-methoxy-2-naphthyl) propionic acid ethylamine salt, working was carried out as above described, to obtain again 60 g of (+)-2-(6-methoxy-2-naphthyl) propionic acid ethylamine salt.

Mother liquors were recycled to give (−)-2-(6-methoxy-2-naphthyl) propionic acid ethylamine salt, after addition of 60 g of (±)-2-(6-methoxy-2-naphthyl) propionic acid ethylamine salt and subsequent seeding.

Cycles can be repeated for an undetermined number of times, carefully controlling volume, water percentages and concetrations of both (±)-2-(6-methoxy-2-naphthyl) propionic acid ethylamine salt and (−)-2-(6- methoxy-2-naphthyl) propionic acid ethylamine salt so as to comply with saturation and supersaturation values, respectively of about 170 and 200 g. For this purpose, it is necessary to carefully analyze the optical quality of each crystallization crop and to calculate the effectively obtained amount of each enantiomer.

Mother solution will be then added with amounts of racemate and possibly of optical enantiomer necessary to respect the initial balance.

Thus, from the reported preparation, the following compounds were obtained:

I resolution 60 g having 91% optical activity, +
II resolution 60 g having 92% optical activity, −
III resolution 70 g having 84% optical activity, +
IV resolution 56 g having 97% optical activity, −
V resolution 60 g having 91% optical activity, + and the related balance is reported in the following table:

TABLE

| CYCLE No. | ENANTIOMER | VOLUME | % K. FISCHER | LEVO SALT | DEXTRO SALT | CRYST. SALT | % OPTICAL PURITY | ADDITIONS |
|---|---|---|---|---|---|---|---|---|
| 1 | + | 2.400 | 16 | 200 | 200 +<br>30 +<br>1 =<br>231 | 60 | 91 | |
| 2 | − | 2.400 | 16 | −2.7<br>197.3<br>30<br>1<br>228.3 | −57.3<br>173.7<br>30<br>200.7 | 60 | 92 | Addition of 60 g of racemic ethylamine salt |
| 3 | + | | | −57.6<br>170.7<br>30<br>200.7 | −2.4<br>201.3<br>30<br>1<br>232.2 | 70 | 84 | Addition of 60 g of racemic ethylamine salt |
| 4 | − | 2.370 | 16.5 | −5.6<br>195.1<br>32<br>4<br>1<br>232.1 | −64.4<br>167.9<br>32<br>199.9 | 56 | 97 | Addition of 64 g of ethylamine racemic salt and 4 g of ethylamine salt levo isomer |
| 5 | + | 2.410 | 16.8 | −55.1<br>177<br>27<br>204 | 0.9<br>199<br>27<br>1<br>227 | 60 | 91 | Addition of 54 g racemic ethylamine salt |
| 6 | − | | | −2.7<br>201.3 | −57.3<br>169.7 | | | |

(c) Analytic controls (1) (+)-2-(6-methoxy-2-naphthyl) propionic acid ethylamine salt 2 g of compound, after drying under vacuum at 60° C. till constant weight, was diluted to a volume of 100 ml with an acetonitrile-acetic acid mixture (70:30). Optical power was determined in a 1 dm cuvette.
$[\alpha]_D^{20°} = 61°$ optical purity 100%

(2) Acetone mother liquors 15 ml of the solution was diluted to 100 ml with an acetonitrile-acetic acid mixture (70:30). Optical activity was determined in a 1 dm cuvette.

$[\alpha]_D^{20°}$ = about 6°, with the algebric sign depending on the cycle going on.

(d) Purification (+)-2-(6-methoxy-2-naphthyl) propionic acid ethylamine salt 30 g of (+)-2-(6-methoxy-2-naphthyl) propionic acid ethylamine salt having optical purity of about 90% ($[\alpha]_{20}^D = +56°$) was dissolved at ebollition in 300 ml of acetone containing about 7% of water. The mixture was cooled to about 35° C. and filtered after 60 minutes stirring. The crystals were washed portionwise with 50 ml of acetone and dried at 60° C. under vacuum.

27 g of the product, having 98–100% optical purity, was obtained.

Racemization (−)-2-(6-methoxy-2-naphthyl) propionic acid ethylamine salt 55 g of (−)-2-(6-methoxy-2-naphthyl) propionic acid ethylamine salt was dissolved in 70 ml of diethylene glycol; the mixture was alkalinized with 47% w/w aqueous potassium hydroxide and heated to 130° C.

Temperature was maintained at 130° C., slowly distilling water and monoethylamine, for about 2 hours; then the mixture was poured into 350 ml of water at about 80° C. and acidified to about pH=4 with aqueous hydrochloric acid.

The obtained suspension was filtered at about 40° C., washing the precipitate with water. 44 g of (±)2-(6-methoxy-2-naphthyl) propionic acid was obtained.

(f) (+)2-(6-methoxy-2-naphthyl) propionic acid 220 g of (+)-2-(6-methoxy-2-naphthyl) propionic acid ethylamine salt was dissolved in 1350 ml of water at 70° C. The obtained completely clear solution was slowly acidified to about pH=5 with 10% w/w hydrochloric acid.

The suspension was cooled to ~30° C. and filtered, the precipitate was washed with water till absence of chloro ions. 180 g of a white product having almost theorical optical activity was obtained.

EXAMPLE 2

Resolution of (+)-2-(6-methoxy-2-naphthyl) propionic acid ethylamine salt 225 g of (±)-2-(6-methoxy-2-naphthyl) propionic acid ethylamine salt (0.820 mole), 222 g of (±)2-(6-methoxy-2-naphthyl) propionic acid (0.96 mole) and 38.5 g of (−)-2-(6-methoxy-2-naphthyl) propionic acid ethylamine salt (0.140 mole) were dissolved in 4000 ml of acetone containing 5.5% of water, under mild reflux.

The mixture was cooled to 45° C., then seeded with 2 g of (−)-2-(6-methoxy-2-naphthyl) propionic acid ethylamine salt and stirred for 2 hours, decreasing temperature to about 35° C. After filtration and washing with 200 ml of anhydrous acetone, 75 g (0.273 mole) of (−)-2-(6-methoxy-2-naphthyl) propionic acid ethylamine salt having 100% titre and $[\alpha] = -57.5°$, equal to 92.7% optical purity, was obtained.

Mother liquors had a volume of 4.000–4.200 ml and K.F. 5.5–6%; 75 g of (±)-2-(6-methoxy-2-naphthyl) propionic acid ethylamine salt was added thereto under mild reflux. After cooling to about 45° C., seeding was carried out with 2 g of (+)-2-(6-methoxy-2-naphthyl) propionic acid ethylamine salt, slowly stirring for 2 hours, letting temperature decrease to about 35° C.

The mixture was filtered and washed with 200 ml of anhydrous acetone to obtain 75 g (0.273 mole) of (+)-2-(6-methoxy-2-naphthyl) propionic acid ethylamine salt, having 100% titre and $[\alpha] = +57.5°$.

Mother liquors were recycled again, keeping volume, K.F. and ethylamine/optical antipode/total acid ratio constant, alternatively obtaining the dextrorotatory and the levorotatory salts.

I claim:

1. A process for the optical resolution of 2-(6-methoxy-2-naphthyl) propionic acid which comprises: at above about 40° C., forming a supersaturated solution in acetone or methanol containing 4–20% water of (±)-2-(6-methoxy-2-naphthyl) propionic acid ethylamine salt, said saturated solution containing the ethylamine salt of one of the enantiomers in excess to the other; cooling said solution to below about 40° C.; initiating the precipitation of the ethylamine salt of the enantiomer in excess by adding a seed quantity of said ethylamine salt; separating said precipitate; reforming said supersaturated solution containing an excess of the ethylamine salt of the other enantiomer by the addition to the mother liquor of an amount of the racemic ethylamine salt equivalent to the separated precipitate; and repeating the seeding to precipitate the ethylamine salt of the other enantiomer.

2. A process according to claim 1 in which the supersaturated solution is an acetone solution containing 15–18% water.

3. A process according to claim 1 in which seeding and precipitation are conducted at about 20°–40° C.

4. A process according to claim 1 in which the ethylamine salts of the enantiomers are converted to their respective acids by treatment with a mineral acid.

5. A process according to claim 4 in which the levo enantiomer is subjected to racemization and recycled to the mother liquor.

6. A process according to claim 1 in which the procedure is repeated any desired number of times.

* * * * *